United States Patent [19]
Fontenot

[11] Patent Number: 5,517,997
[45] Date of Patent: May 21, 1996

[54] TRANSILLUMINATION OF BODY MEMBERS FOR PROTECTION DURING BODY INVASIVE PROCEDURES

[75] Inventor: Mark G. Fontenot, Lafayette, La.

[73] Assignee: Gabriel Medical, Inc., Lafayette, La.

[21] Appl. No.: 305,296

[22] Filed: Sep. 15, 1994

[51] Int. Cl.⁶ ............................................. A61B 5/00
[52] U.S. Cl. ..................... 128/664; 128/665; 128/899
[58] Field of Search ................................. 128/664–665, 128/899; 606/32, 34, 41

[56] References Cited

U.S. PATENT DOCUMENTS

| | | |
|---|---|---|
| 4,114,601 | 9/1978 | Abels . |
| 4,248,214 | 2/1981 | Hannah et al. . |
| 4,459,990 | 7/1984 | Barnea . |
| 4,782,819 | 11/1988 | Adair . |
| 4,784,149 | 11/1988 | Berman et al. . |
| 4,821,731 | 4/1989 | Martinelli et al. . |
| 4,852,579 | 8/1989 | Gilstad et al. . |
| 4,856,527 | 8/1989 | Karcher et al. . |
| 4,898,175 | 2/1990 | Noguchi . |
| 4,978,049 | 12/1990 | Green . |
| 4,981,138 | 1/1991 | Deckelbaum et al. . |
| 4,994,066 | 2/1991 | Voss . |
| 5,012,809 | 5/1991 | Shulze . |
| 5,040,715 | 8/1991 | Green et al. . |
| 5,071,430 | 12/1991 | de Salis et al. . |
| 5,108,407 | 4/1992 | Geremia et al. . |
| 5,139,025 | 8/1992 | Lewis et al. . |
| 5,168,873 | 12/1992 | Seifert et al. . |
| 5,190,059 | 3/1993 | Fabian et al. . |
| 5,211,165 | 5/1993 | Dumoulin et al. . |

FOREIGN PATENT DOCUMENTS 2102127  1/1983  United Kingdom .

*Primary Examiner*—Ruth S. Smith
*Attorney, Agent, or Firm*—Howard L. Rose

[57] ABSTRACT

An apparatus and method for protecting a body member from damage during a body intrusive procedure in a region adjacent the body member to be protected includes a source of infrared energy introduced into a light guide that is introduced into the body member to be protected; a source of visible light is introduced into the region, this latter source being pulsed at the frame rate of a monitor energized by an infrared sensitive video camera that receives light from such region, the camera being sensitive to infrared energy as well as visible light. In another embodiment of the invention both sources are pulsed in alternation so that the images produced by the different sources are basically emphasized in alternation. A signal source for producing audible and/or visual signals may be provided with a light guide to view the region under investigation. The signal source may be synchronized with the infrared source to protect against false signals produced by the visual light.

20 Claims, 3 Drawing Sheets

TRANSILLUMINATION OF BODY MEMBERS FOR PROTECTION DURING BODY INVASIVE PROCEDURES

RELATED APPLICATIONS

This application is related to the present Applicant's application Ser. No. 08/190,516 filed Feb. 2, 1994 now U.S. Pat. No. 5,423,321 for "Detection of Artatomic Passages Using Infrared Emitting Catheter".

FIELD OF THE INVENTION

The present invention relates to methods and apparatus for transillumination of various parts of a living body to avoid damaging such parts during an invasive procedure and more specifically to the use of two different light sources in such procedures.

BACKGROUND OF THE INVENTION

Although the present invention is described in connection with protection of a ureter during a surgical procedure this is done merely for purposes of ease of illustration; the invention being useful for protection of various body parts lying adjacent a region subjected to an invasive procedure.

Currently practiced methods and devices used to transilluminate the ureters to permit ready location and thus protection of the ureter during endoscopic procedures require the cystoscopic placement of a catheter housing a fiber optic light guide into the lumen of the ureter. The distal portion of the fiber optic light guide is treated to allow light preferably to emit circumferentially from the wall of the fiber. The proximal end of the fiber is coupled to a visible light source. A second light source is coupled to an endoscope and introduced into the surgical site.

Light detection of the transilluminated ureter using typical illuminating catheters such as the Bush DL™ Ureteral Illuminating Catheter Set coupled to a light source during endoscopic procedures is facilitated with a camera. The camera projects the detected image of the transilluminated ureter on a monitor for visualization. Sufficient light from the predicate devices must traverse the ureter and overlying tissues with ample intensity to penetrate surrounding tissue and to overcome the illuminated field from the endoscopic light for the camera to detect light emanating from the transilluminated ureter. In the presence of the normally illuminated operative field from the endoscopic light, the camera frequently cannot detect light emanating from the transilluminated ureter. In an attempt to optimize and intraoperatively improve the performance of their device, Cook Urological, Inc. suggests that it may be necessary to dim or eliminate the endoscopic light illuminating the surgical field.

OBJECTS OF THE INVENTION

It is an object of the present invention to permit ready detection of preferably an infrared light source as well as a more standard light source as opposed to an endoscopic light source during an invasive procedure in a region of a body adjacent the ureter or other body member to be protected.

It is another object of the present invention to provide a system and method permitting ease of discrimination of light energy emanating from a body member to be protected during an invasive procedure adjacent said body member from light introduced to illuminate the region of the procedure adjacent such body member.

It is yet another object of the present invention to protect a body member during a surgical procedure adjacent thereto by emitting modulated electromagnetic radiation from such member to permit ready detection of such radiation in the presence of light illuminating the area of the procedure.

Yet another object of the present invention is to emit continuously, electromagnetic energy from a body member to be protected during an invasive procedure in a region adjacent thereto and to pulse a light employed to illuminate the region during the procedure.

Another object of the present invention is to synchronize emissions of electromagnetic energy from a body to be protected during a surgical procedure in a region adjacent thereto with emission of light into the region for illumination thereof.

Still another object of the present invention is to synchronize a camera shutter with periodic emission of light into a region being subjected to an invasive procedure with periodic emission of detectable energy from a body member to be protected from injury during such invasive procedure.

Yet another object of the present invention is to couple an optic fiber employed to detect light emitted by a source located in a body part to be protected, to a surgical instrument to be inserted into a body cavity in which a procedure is to be conducted.

BRIEF DESCRIPTION OF THE PRESENT INVENTION

In a first embodiment of the invention an endoscopic light source is pulsed while continuous emissions of infrared energy are provided from a body member to be protected, such as a ureter, duct, colon, blood vessel or other body member. The endoscopic light source is pulsed on at every other frame or half frame of an interlaced display on a monitor so that one half of the interlaced frame displays both the member to be protected and the area of the operation and the next half of the interlaced frame displays only the emission from the body member to be protected.

In a second embodiment of the invention a light source disposed in a body member to be protected during surgery or other invasive procedure in the region of said body member, is pulsed on when visible light projected into such region is off and vice versa. The on-time of the source in the body member is synchronized with operation of the shutter of a video camera employed to project an image of a body member on a monitor. In this arrangement, the body member and the region of the invasion of the body are displayed in alternate frames on the monitor.

In another embodiment of the invention, the light fiber employed to detect light in the surgical area is secured to a surgical instrument to be inserted into and used in such area. The fiber may be carried by a sleeve slipped over the instrument which may be a scissor, a stapler, or the like. The fiber may be a forward looking or side looking fiber as determined by the requirements of the surgical site.

In still another embodiment of the invention, an audible alarm can be used in the former two embodiments of the invention and is synchronized with the infrared light source. Thus such alarm will not respond to infrared energy of the endoscopic light source and the level of infrared energy to produce detection may as a result be reduced to provide information at an even greater distance from the member to be protected than might otherwise be the case.

All three of the above systems may be operated with NTSC, PAL or SECAM video systems so that as appropriate frames may be interlaced as indicated hereinafter.

DETAILED DESCRIPTION OF THE PRESENT INVENTION

Figure 1:
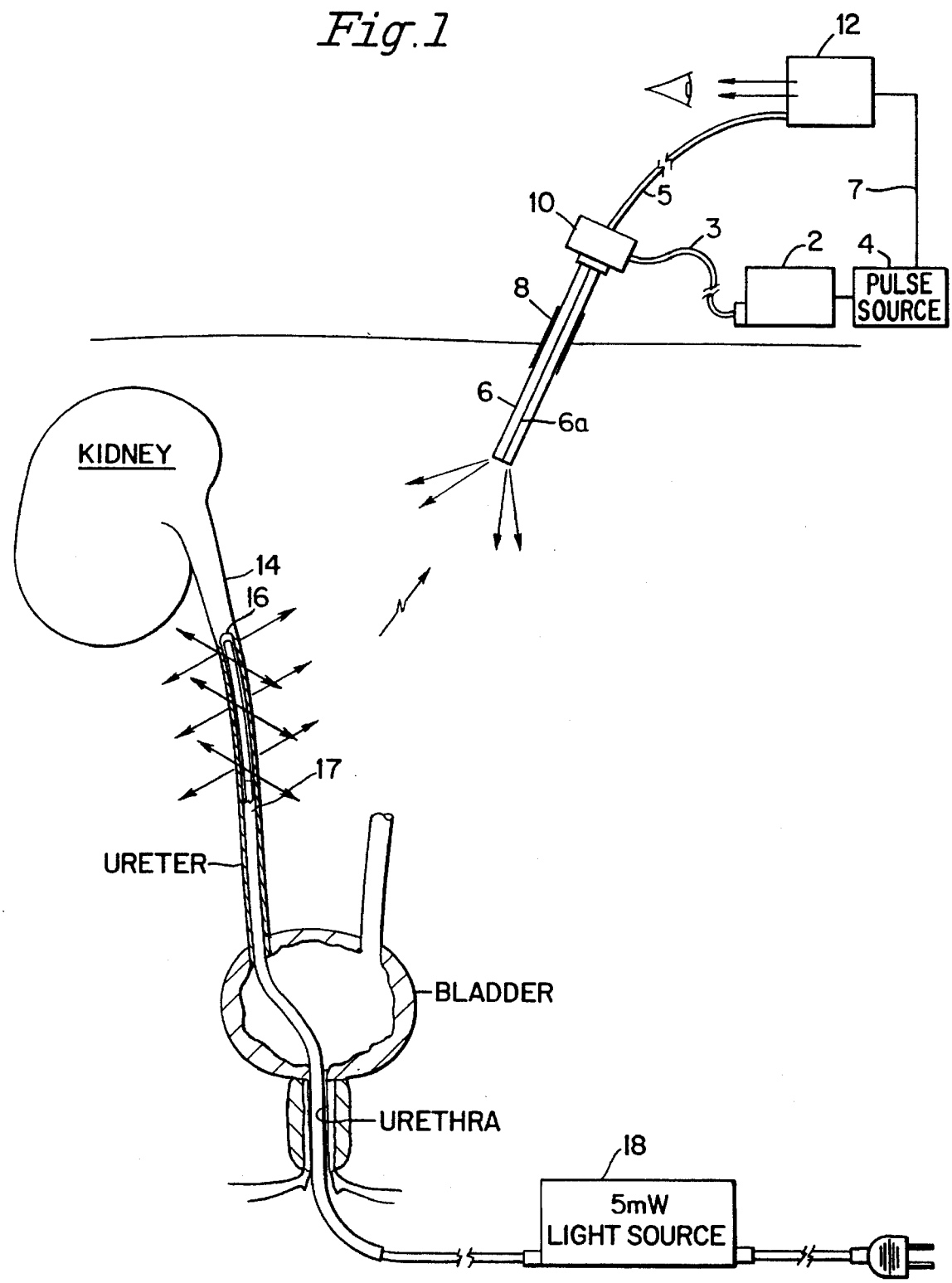
FIG. 1 illustrates a first embodiment of the present invention.

Referring specifically to FIG. 1 of the accompanying drawings, there is illustrated a diagram of a system employing a pulsed laparoscopic visible light source 2. The source 2 is turned on and off by a source of energizing pulses 4 at a rate that is synchronized with the frame rate of a monitor 12 via lead 7.

The light source 2 provides light via a fiber optic bundle 3 to a light guide 6 in this instance illustrated as associated with a trocar 8 and via the light guide into the region of the body to be illuminated. The distal end of the light guide 6 is located internally of a body in a region to be illuminated or upon which a surgical procedure is to be performed. The proximate end of a second light guide 6a is connected to supply light to the charge coupled device of a laparoscopic camera 10 that in turn processes the signals and supplies the processed signals to a monitor 12 via a fiber optic bundle 5. Standard endoscopic optics directs light supplied by the source 2 and reflected by the body tissue in such regions directly to the monitor where the signals are processed and displayed. Normally such cameras have a filter over the sensing chip to block out infrared. In this instance such filter is not used so that the camera can respond to energy of such wavelengths transmitted thereto via fiber 6a.

The entry of the trocar into a body is adjacent to an organ, etc. to be protected from damage during a procedure. In the illustrated example of FIG. 1, the body member to be protected is a ureter designated by reference numeral 14. A catheter 16 is inserted into the ureter and a fiber optic light guide 17 is inserted into the catheter and may be conditioned to emit infrared energy in all directions as fully disclosed in said Related Application, the full disclosure of which is incorporated by reference. The light energy is supplied by a 150 W to 300 W infrared or visible range light source 18 coupled to the light guide 17.

In operation of the system, the continuous infrared energy is transmitted to the light guide 6 and thence to the video camera which provides an image on the screen of the monitor 12. The intermittent visual light is also displayed on the monitor thereby displaying a view of the region being investigated but the display of the infrared image is stronger and readily locates the ureter in this case in the field of view appearing on the monitor. During the period the source 2 is turned off, the display of the ureter light source clearly predominates.

Figure 2:
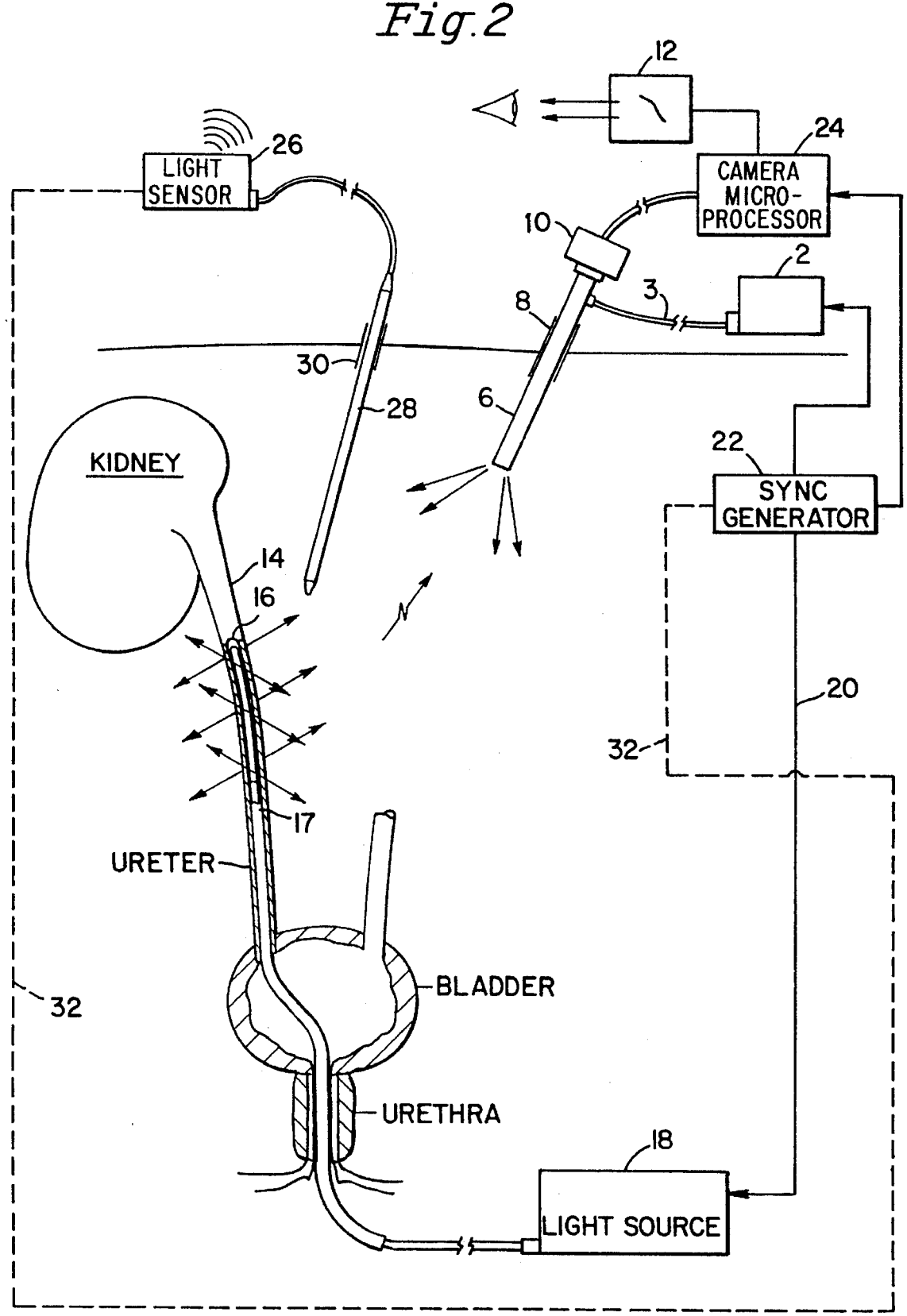
FIG. 2 illustrates a second and a third embodiment of the present invention.

Referring to FIG. 2 there is illustrated a second embodiment of the present invention employing synchronization of various elements of the system. Again light source 18 supplies infrared energy to the fiber optic light guide 17 but the source 18 is pulsed via a lead 20 from a sync generator 22. The sync generator 22 provides pulses to a camera microprocessor 24 that controls the shutter of the camera 10 and the sweep of the monitor 12. The sync generator also controls the energization of the light source 2. Further there is provided an infrared light sensor 26 that produces an audible sound (and/or visual display) whenever infrared is transmitted thereto via a light guide 28 also introduced into the region of interest via a trocar 30.

Note in FIG. 2, a dashed line 32. This line comes from the sync generator 22 and pulses the light sensor 26 in synchronism with the light source 18. With such procedure, the sensor 26 cannot be triggered by light from the endoscope source 2 and a low threshold may be used so that infrared emission from the ureter probe may be detected at a greater distance from it than would be possible otherwise.

In operation, the sync generator 22 alternates energization of the light sources 2 and 18 so that the catheter light is on when the endoscope light source 2 is off and vice versa. Such operation provides great flexibility of the display on the monitor. If the camera is turned on only when the source 18 is energized then only the ureter is displayed. If the camera is turned on only when the endoscopic light source is energized then only the surgical area is displayed (not a good practice if a body member is endangered by the procedure). Alternatively and preferably the system is established such that the camera is turned on with each light source so that with proper synchronization and preferably the use of an NTSC system the two areas are displayed in alternate interlaced frames on the monitor.

The probe 28 and associated circuitry provide an audible signal (light may be employed) the intensity of which varies with proximity of the probe 28 to the ureter. Thus the location of the ureter may be determined with greater precision than may be possible with the probe 6—monitor 12 system without the use of 30 pictures. The probe 28 shows on the monitor and the relative position of the surgical instrument relative to the ureter is more readily determinable by the position of the instrument relative to the probe 28.

Figure 3:
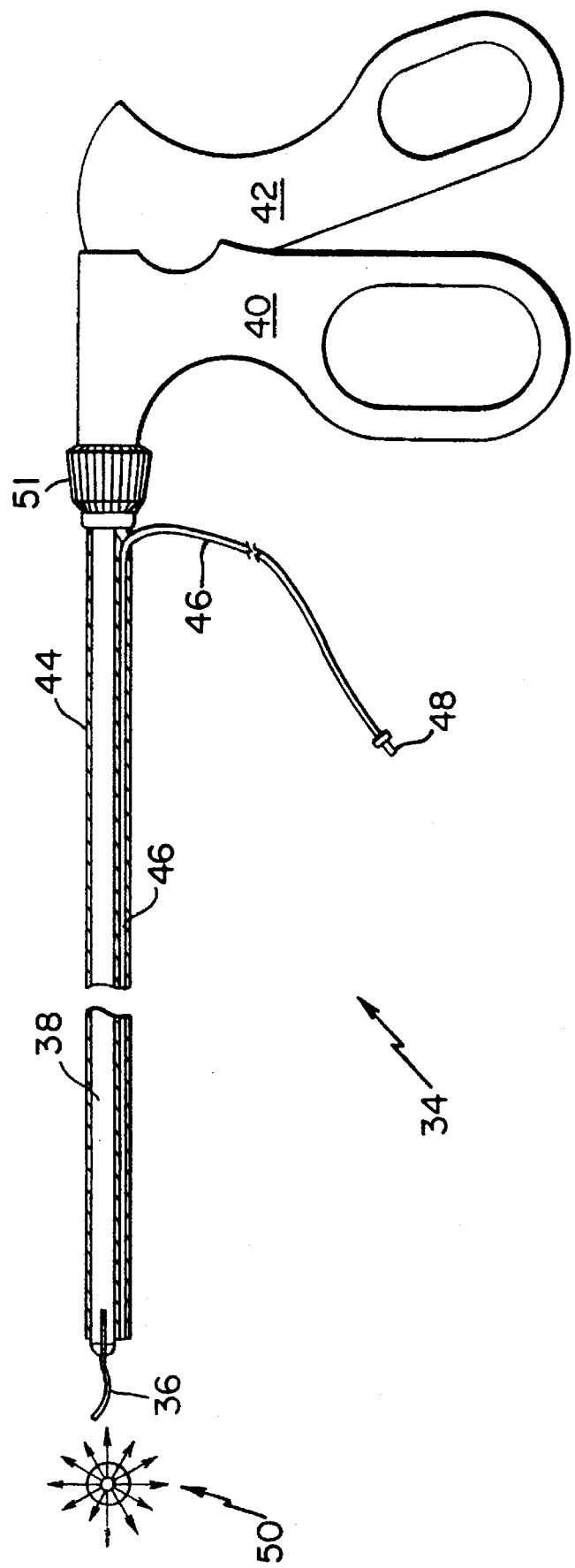
FIG. 3 illustrates a surgical scissor with a fiber bearing sleeve disposed about the instrument.

Referring to FIG. 3 of the accompanying drawings, there is illustrated a surgical scissor generally designated by the reference numeral 34. The two blades of the scissor, only one, blade 36 being illustrated, are carried at the end of a hollow shaft 38 having the operating mechanism for the scissor disposed therein. The scissor is actuated by squeezing together two hand grip members 40 and 42.

A sleeve 44 is slipped over the shaft 38 and carries an optical fiber 46 in a passage formed in the sleeve. An end 48 of the fiber is connected to a light sensor such as camera 10 of FIG. 2 or other suitable sensor such as illustrated in the aforesaid application, Ser. No. 08/190,516 filed Feb. 2, 1994.

The element designated 50 in FIG. 3 is the infrared emitting fiber in the organ to be protected, for instance, a ureter. The fiber 46 illustrated in FIG. 3 is a forward looking fiber but could also be a side looking fiber.

Following is a Truth Table, Table 1, of operation with the system of FIG. 2, with the camera shutter open. When both lights are on continuously the response relative to both of the light sources by the monitor and the audible source is marginal. The monitor display does not provide sharp definition of either area to be observed, the light from each being confusing.

When only the catheter source is "on" the display of the ureter, in this instance, is clear and sharp and the audible response can be relied upon since infrared from the endoscopic source does not interfere with the signal generator 26. When only the endoscopic source is "on" the image of the ureter is not detected but is at least partially displayed from the preceding half frame. The same is true relative to endoscopic display.

If the threshold on the audible detector is low enough an audible signal may be detected even though the infrared source is off. This problem may be addressed by pulsing the audible signal source "on" via lead 32 only when the infrared source is energized. Under these circumstances there is no problem with the visual light and the threshold can be set relatively low on this detector.

When the camera shutter is closed the Truth Table 2 applies. Specifically only the audible signal generator 26 is operative and the response is the same as in the table above.

TABLE 1

Truth Table outlining the performance of the synchronized dual light sources used to transilluminate the ureters during endoscopic surgery. The camera shutter is open.

| Catheter Light Source | ON | ON | OFF |
|---|---|---|---|
| Endoscope Light Source | ON | OFF | ON |
| Visual Detection on Monitor | Marginal Not Efficient | YES | NO |
| Audible Detection using Light Probe | Marginal Not Efficient | YES | NO but possible |
| Audible Detection Using Pulsed Light Probe | Marginal Not Efficient | YES | NO |

TABLE 2

Truth Table outlining the performance of the synchronized dual light sources used to transilluminate the ureters during endoscopic surgery. The camera shutter is closed.

| Catheter Light Source | ON | ON | OFF |
|---|---|---|---|
| Endoscope Light Source | ON | OFF | ON |
| Visual Detection on Monito | NO | NO | NO |
| Audible Detection using Light Probe | Marginal Not Efficient | YES | NO but possible |
| Audible Detection Using Pulsed Light Probe | Marginal Not Efficient | YES | NO |

The pulsing of the infrared source greatly enhances the ability of the surgeon or other health care operative to distinguish between light emanating from the infrared source and visual light reflected from the tissue illuminated by light from an endoscopic or ambient light source.

In furtherance of this concept, the audible signal may be modulated with an identifiable signal to insure that the sound does not simply fade into the background of consciousness. For instance, a 1500 cycle per second tone can be imposed on the output during each "on" cycle. Also this approach reduces the effect of noise from the light sources. The 1500 Hz signal may be applied to a 50% duty cycle 12 KHz square wave.

The audible signal generator could also be a visual light source that would blink at a rate that varies with proximity of the probe to the body member to be protected.

Typical specifications for this system are:

1. A 5 mW infrared LED or two variable 250 mW infrared laser diodes.

2. An infrared emitting segment of 20 to 25 cm.

3. An ST type optical connector on the proximate end of the light detector probe. Both the light probe and guide are manufactured by Ethox Corporation.

4. Government regulations for a Class I laser required that the power emitted from the fiber optic light guide should not exceed 60.8 µW from the hottest point on the fiber at a distance of 20 cm through a 7 mm operation.

5. Ureteral catheter—65 cm long with an O.D. of 2.3 mm and three holes for drainage from TFX Medical.

6. The light guide is an Eska Fiber from Mitsubishi.

7. Light source spectrum of 620 nm to 1,000 nm.

8. The camera is a Model 510(k) manufactured by Envision Medical Corporation of Santa Barbara, Calif.

The device disclosed herein will often be sold as an article of commercial in which the various elements will be sold as a package. Such could include the light source, the fiber for insertion into an organ, vessel or the like, a catheter which may or may not be used with the aforesaid light fiber, a camera, camera microprocessor, sync generator light source, light sensor, pulse generator and/or audible or visual proximity sensor with ancillary equipment as required. The article may be that illustrated in FIG. 1 or FIG. 2 and may or may not include the sleeve of FIG. 3.

Once given the above disclosure, many other features, modifications and improvements will become apparent to the skilled artisan. Such features, modifications and improvements are, therefore, considered to be a part of this invention, the scope of which is to be determined by the following claims.

What is claimed is:

1. An apparatus for reducing the danger of damage to a body member located in a region of an intrusive procedure in a body in which the body member is located comprising, a fiber optic light guide insertable into the body member to be protected, a source of infrared energy having means for introducing such energy into said light guide, said light guide having a region for emitting said infrared energy along axes transverse to said light guide, a source of visible light energy, means for introducing said visible light energy into said region of said light guide, means for pulsing at least one of said sources of light energy, and means for locating said body member by detecting said infrared energy.

2. The apparatus according to claim 1 further comprising means for energizing said sources in alternation.

3. The apparatus according to claim 1 further comprising a signal device for stimulating a human sensory response, said signal device having a probe insertable into the body adjacent an operation site for transmitting infrared light energy emitted from said light guide to said signal device, and means for rendering said signal device operative only when said infrared energy source is energized.

4. The apparatus according to claim 3 wherein said signal device includes means for producing an audible sound..

5. The apparatus according to claim 1 further comprising a camera responsive to infrared energy, a light guide for directing energy from said sources to said camera.

6. The apparatus according to claim 5 wherein said camera is a video camera, and a scanning monitor for receiving signals from said video camera and displaying said signals on the screen of the monitor.

7. The apparatus according to claim 6 further comprising means for pulsing said sources on and off in alternation, and means for synchronizing the pulsing of said sources with the scan of said monitor.

8. The apparatus according to claim 7 further comprising means for operating said monitor on the NTSC system and images produced when each said source is energized are displayed alternately by the scans of said monitor.

9. The apparatus according to claim 7 further comprising means for operating said monitor on the PAL system and images produced when each said source is energized are displayed alternately by said monitor.

10. The apparatus according to claim 7 further comprising means for operating said monitor on the SECAM system and images produced when each said source is energized are displayed by said monitor.

11. The apparatus according to claim 1 further comprising a camera responsive to infrared energy, means for directing infrared energy to said camera, said means for directing infrared energy further directing visible light reflected from said region to said camera.

12. The apparatus according to claim 11 further comprising means for energizing said sources alternately and successively.

13. The apparatus according to claim 9 wherein said means for detecting infrared energy produces a sound upon detection of such energy.

14. The apparatus according to claim 1 further comprising a camera responsive to light energy, a light guide for directing energy from said sources to said camera.

15. An apparatus according to claim 1 further comprising a sleeve disposable about a surgical instrument to be inserted into said region and insertable therewith, said sleeve having means for securing said means for locating said body member to such instrument for insertion into such region with such instrument.

16. The apparatus according to claim 1 further comprising a signal device for stimulating a human sensory response, said signal device having a probe insertable into the body adjacent an operation site for transmitting light energy to said signal device.

17. An apparatus for reducing the danger of damage to a body member located in a region of an intrusive procedure in a body in which the body member is located comprising, a fiber optic light guide insertable into the body member to be protected, a source of infrared light energy having means for introducing such energy into said light guide, said light guide having a region for emitting said infrared energy along axes transverse to said light guide, a source of visible light, means for introducing said visible light into said region, means for pulsing said source of light energy, and means for locating said body member by detecting said light energy.

18. An article of commerce comprising a light guide insertable into a cavity in an animal, said light guide having means to emit light from a predetermined region thereof, a source of light having means for directing light into said light guide, a light detector capable of detecting light emitted by said light guide, and said light detector having means for indicating the proximity of said means for emitting light to said light guide.

19. An article of commerce according to claim 18 wherein said source emits infrared energy, and wherein said light detector comprises a camera sensitive to infrared energy.

20. The method of locating or reducing the danger during surgery or other invasion of a body of causing injury to body members into which a catheter is insertable comprising the steps of inserting a catheter into the body member, inserting an elongated infrared light guide having a region that emits such light into the catheter, directing infrared light energy into the light guide, directing visible light into a region adjacent the body member, pulsing the infrared light energy and the visible light in alternation, and indicating the proximity of an ongoing surgical procedure to the body member by determining the intensity of the infrared radiation exiting the body member at the surgical site.

* * * * *